United States Patent [19]
Braddock et al.

[11] Patent Number: 5,409,498
[45] Date of Patent: Apr. 25, 1995

[54] ROTATABLE ARTICULATING ENDOSCOPIC FASTENING INSTRUMENT

[75] Inventors: Charles K. Braddock; Thomas W. Huitema, both of Cincinnati; David Stefanchik, Mason; Kenneth S. Wales, Cincinnati, all of Ohio

[73] Assignee: Ethicon, Inc., Somerville, N.J.

[21] Appl. No.: 971,653

[22] Filed: Nov. 5, 1992

[51] Int. Cl.⁶ ............................................. A61B 17/00
[52] U.S. Cl. ..................... 606/143; 606/142; 606/139; 227/901
[58] Field of Search ............... 606/142, 143, 139, 151, 606/205–207; 227/175–176, 178–179, 181, 901, 19

[56] References Cited

U.S. PATENT DOCUMENTS

| | | | |
|---|---|---|---|
| 2,507,710 | 5/1950 | Grosso | 606/205 |
| 3,234,636 | 2/1966 | Brown | 606/143 |
| 4,427,008 | 1/1984 | Transue | 606/143 |
| 4,452,376 | 6/1984 | Klieman et al. | 606/143 |
| 4,562,839 | 1/1986 | Blake, III et al. | 606/143 |
| 4,566,620 | 1/1986 | Green et al. | |
| 4,728,020 | 3/1988 | Green et al. | |
| 4,869,414 | 9/1989 | Green et al. | |
| 4,872,456 | 10/1989 | Hasson | 606/207 |
| 5,042,707 | 8/1991 | Tahari | |
| 5,084,057 | 1/1992 | Green et al. | 606/142 |
| 5,100,420 | 3/1992 | Green et al. | |
| 5,125,553 | 6/1992 | Oddsen et al. | 227/175 |
| 5,174,276 | 12/1992 | Crockard | 606/142 |
| 5,271,543 | 12/1993 | Grant et al. | 227/179 |
| 5,275,608 | 1/1994 | Forman et al. | 606/205 |
| 5,289,963 | 3/1994 | McGarry et al. | 606/142 |

FOREIGN PATENT DOCUMENTS

| | | | |
|---|---|---|---|
| 0541987 | 5/1993 | European Pat. Off. | A61B 17/00 |
| WO88/01486 | 3/1988 | WIPO | 606/143 |

Primary Examiner—Stephen C. Pellegrino
Assistant Examiner—J. A. Schmidt
Attorney, Agent, or Firm—Paul A. Coletti

[57] ABSTRACT

A new and improved endoscopic surgical instrument. The business head of the instrument is rotatable about its longitudinal axis and is also articulatable in and out of longitudinal alignment with the longitudinal axis of the instrument.

43 Claims, 17 Drawing Sheets

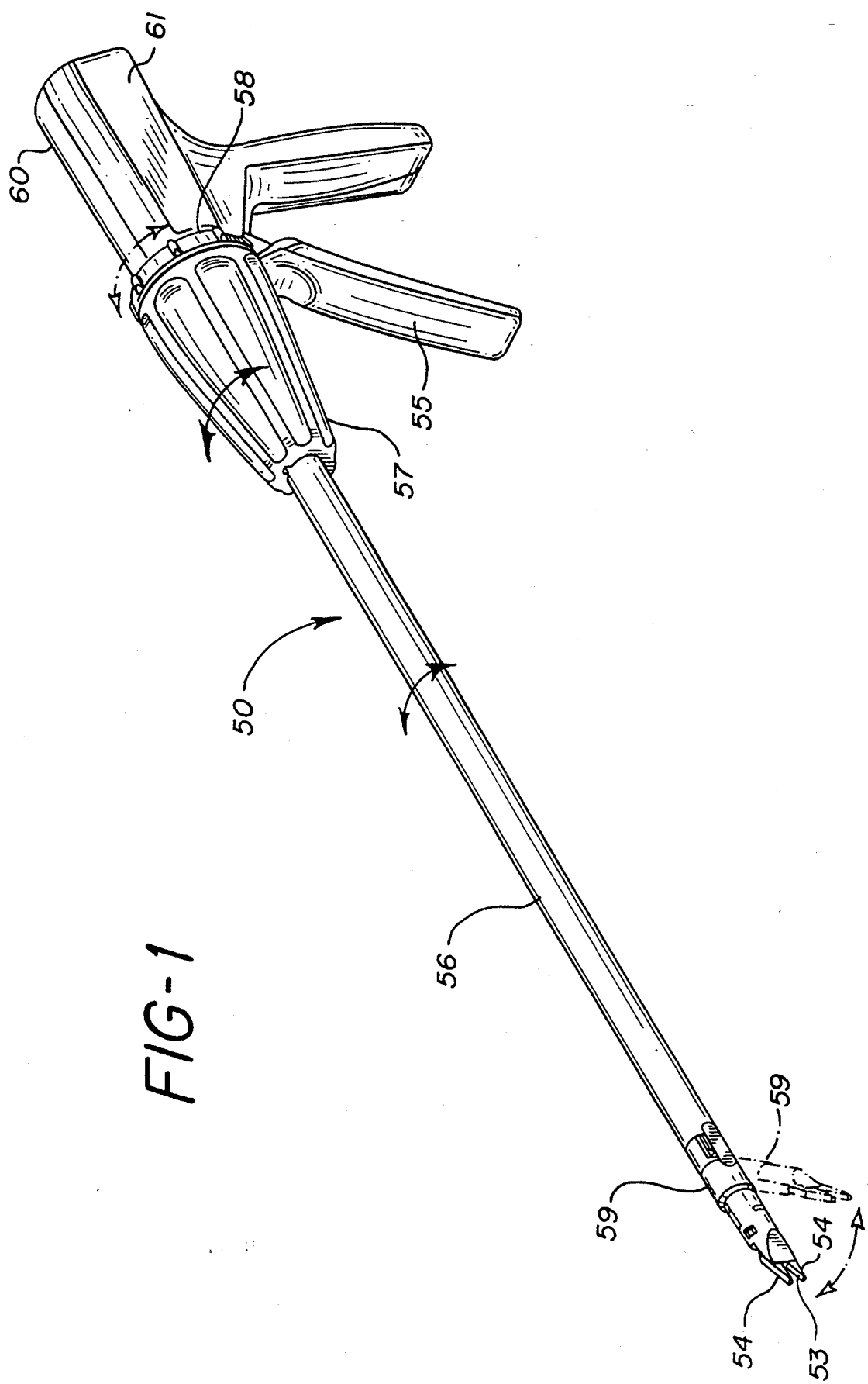

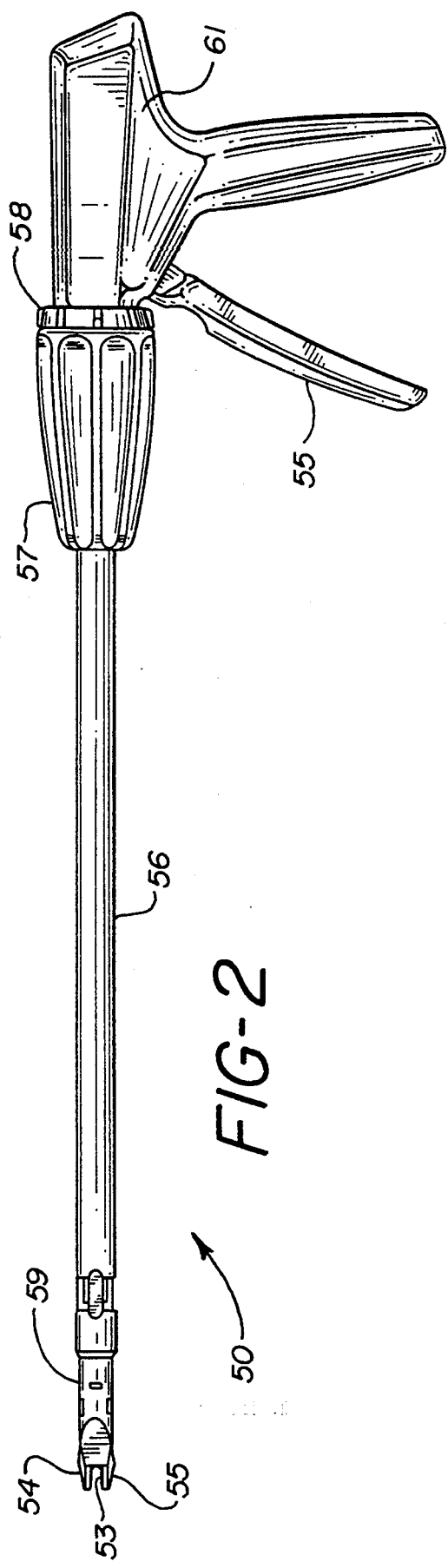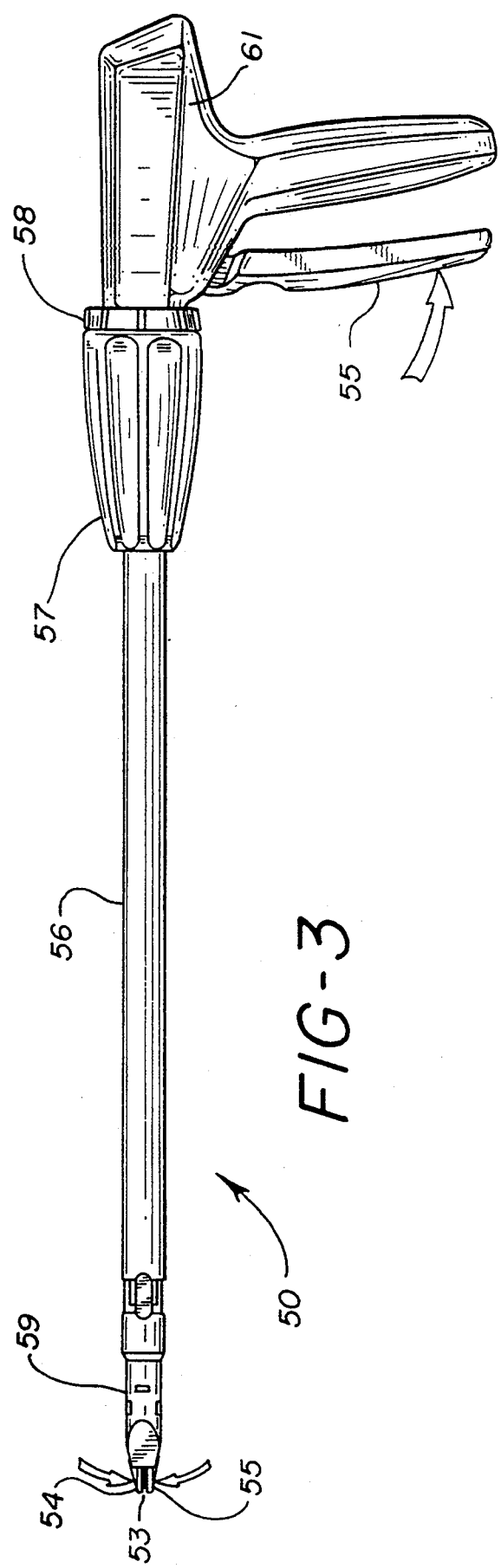

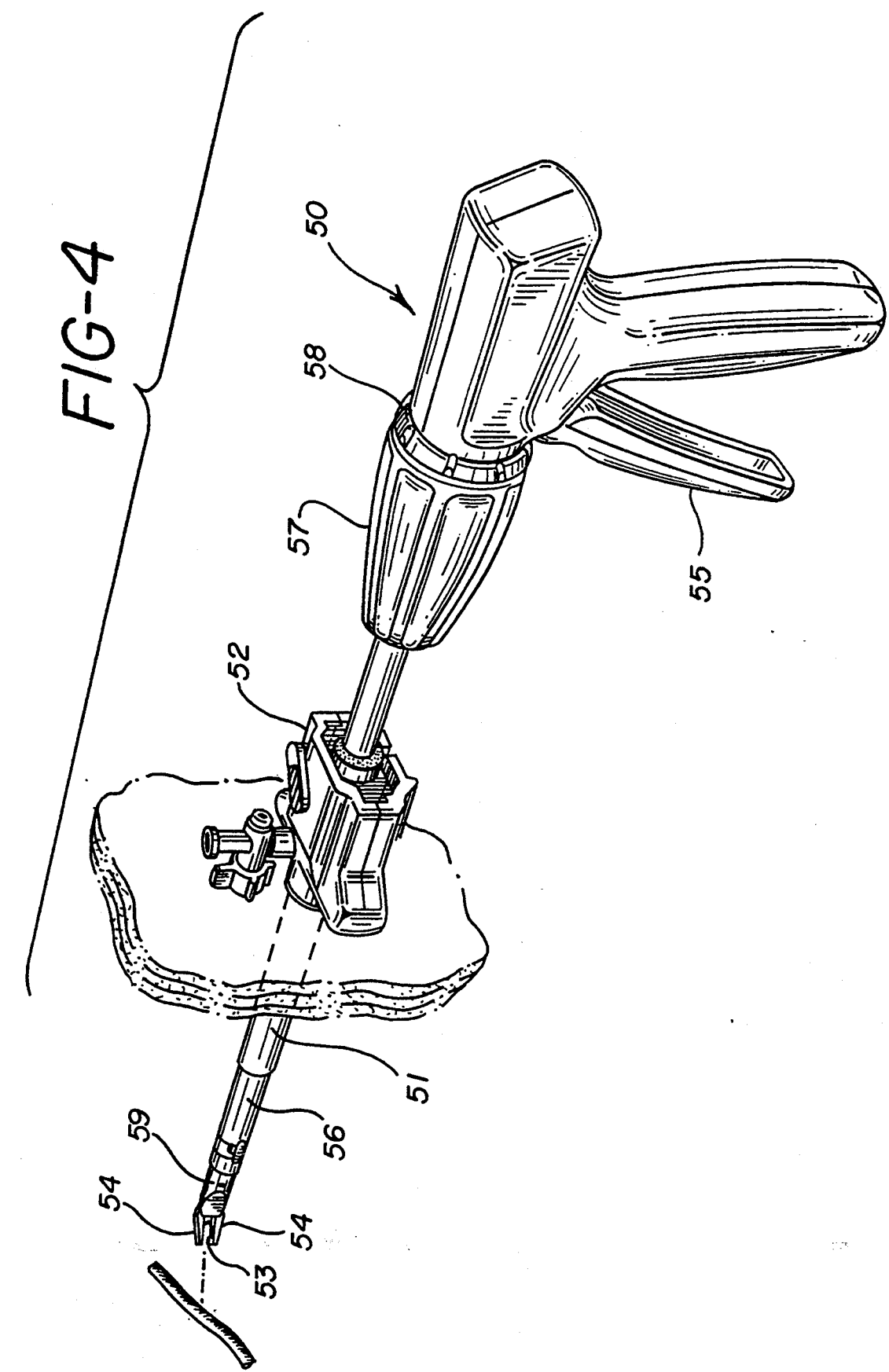

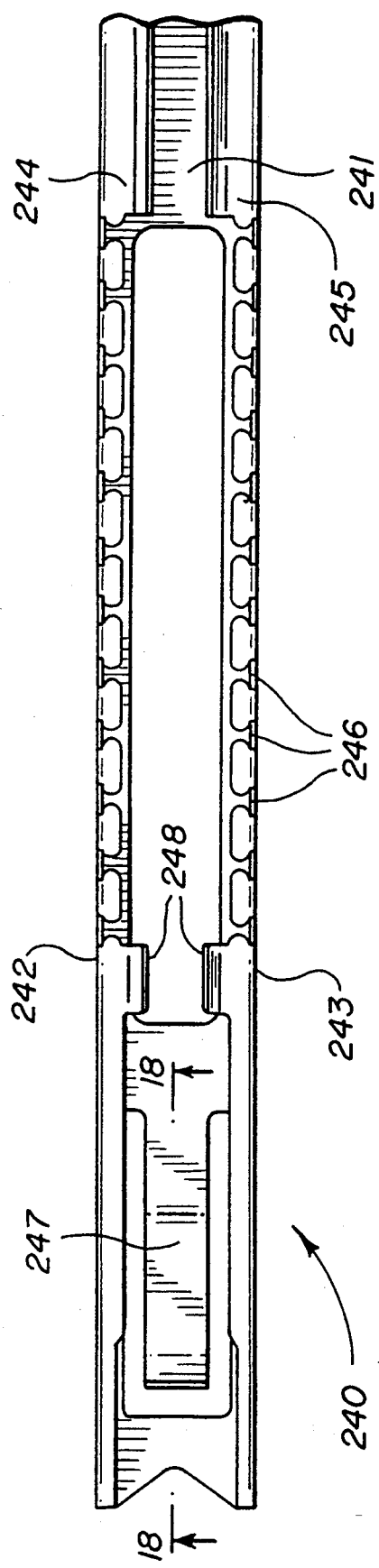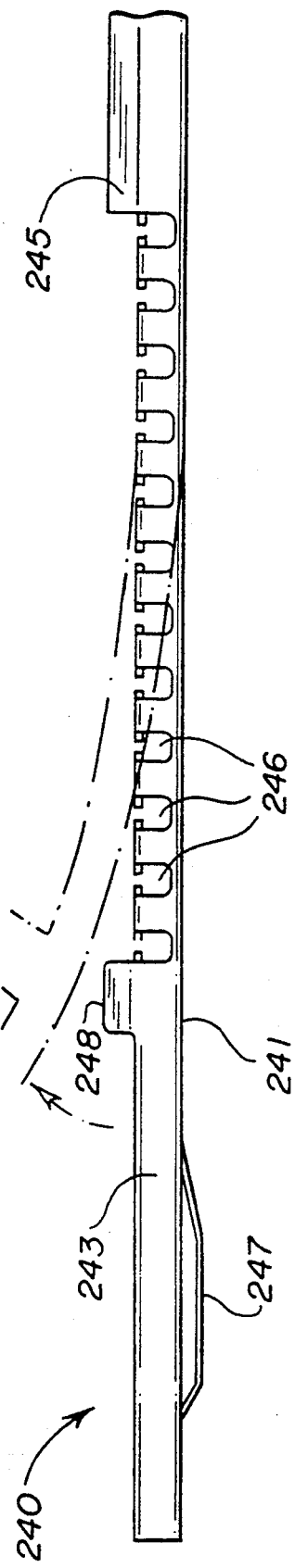

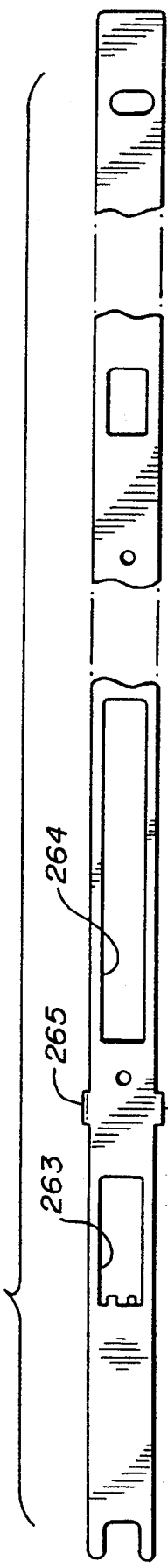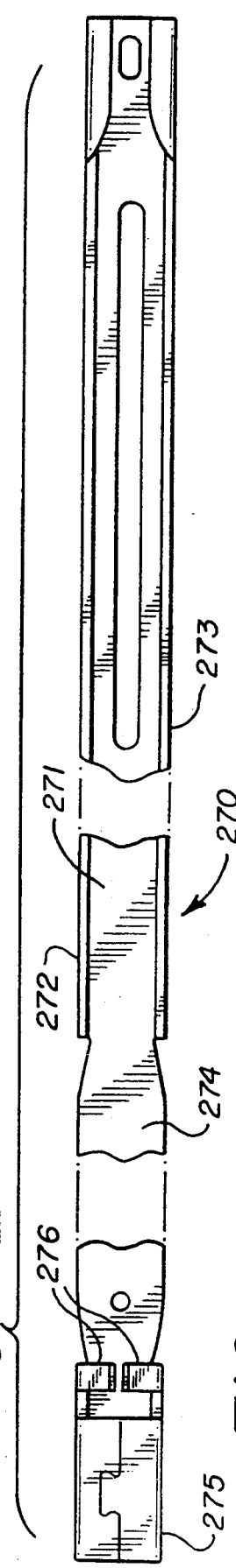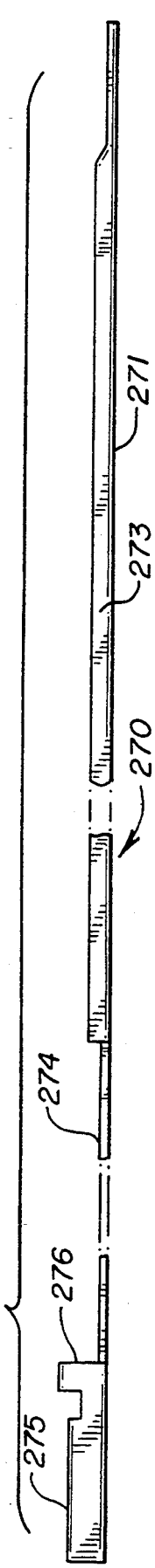

ROTATABLE ARTICULATING ENDOSCOPIC FASTENING INSTRUMENT

FIELD OF INVENTION

This invention relates to a rotatable and articulating endoscopic fastening instrument for applying fasteners to body tissue. More specifically, this invention relates to a rotatable articulating endoscopic multiple clip applier for applying surgical clips to vessels to ligate the vessels.

BACKGROUND OF THE INVENTION

Endoscopic surgery has been gaining wide acceptance as an improved cost effective technique for conducting certain surgical procedures. In endoscopic surgery, a trocar, which is a pointed piercing device, is sent into the body with a cannula placed around the trocar. After the trocar accomplishes piercing of the abdominal walls it is removed and the cannula remains in the body. Through this cannula, endoscopic procedures are possible. Often, multiple openings are produced in the body with a trocar so that an endoscopic instrument may be placed in one cannula, appropriate viewing mechanisms placed in another cannula and fiber optics for illuminating the surgical field placed in yet another cannula. Generally, these endoscopic procedures take place with insulfation. As more is learned about endoscopic procedures and more instruments developed, the type of procedures that may be performed endoscopically will increase. Presently, typical procedures are gall bladder removal, tissue repair, and various sterilization procedures.

One class of instruments used in endoscopic surgery are the fastening instruments such as staplers, clip appliers and the like. As can be appreciated, in an endoscopic procedure in that the instrument is placed down the cannula into the surgical field, the mobility and the access that instrument will have within the field is often quite limited. These type of instruments may not be able to reach desired areas because that area is behind other tissue or may be too far out of line with the head of the instrument. Often in some endoscopic procedures, it may be desirable to get to a vessel which is disposed behind an organ. While some of these problems may be overcome by appropriately placing the cannula, clearly there are limits on the mobility and the accessibility of the business head of endoscopic instruments.

The endoscopic instruments of the present invention overcome these problems in that they provide for considerably improved mobility of the business end of the instrument within the surgical site. Furthermore, the endoscopic instruments of the present invention provide greatly improved accessibility to tissue within the surgical site. Also, the endoscopic instruments of the present invention allow a surgeon to work on tissue that is disposed behind other tissue or in back of an organ.

SUMMARY OF THE INVENTION

The endoscopic surgical instrument of the present invention has a rotatable endoscopic portion and an articulatable endoscopic head or business end of the instrument. The instrument comprises a handle portion which contains appropriate actuating means. Extending distally from this handle portion is an elongated tubular portion. Preferably this tubular portion is hollow and contains the mechanisms for feeding and applying fasteners which is accomplished by the head of the instrument. At the distal end of the elongated portion is the fastener applying head. The fastener applying head is hingedly attached to the elongated tubular portion. In preferred embodiments of the present invention, the head is pivotally attached to the distal end of the elongated tubular portion. The instruments also include articulating means for moving the head of the instrument in and out of longitudinal alignment with the distally extending elongated portion. In preferred embodiments of the instrument of the present invention, the articulating means is attached to the head of the instrument distally of the hinged or pivot attachment of the head to the elongated portion. In certain embodiments of the instruments of the present invention, there is included means for storing a plurality of fasteners. The instruments of the present invention include means for feeding fasteners to the head of the instrument and actuating the head of the instrument to apply the fasteners. The multiple fastener instrument of the present invention provides means for storing fasteners within the elongated tubular portion and means for feeding the fasteners through the articulation area to the fastener head. This allows for the storage of a considerable number of fasteners. While the head of the instrument is articulatable, it is also preferred that the head of the instrument and the elongated tubular portion be rotatable. This provides considerable mobility to the head of the instrument and allows for an increased area of access within the surgical site. The head of the instrument may be both articulated in and out of longitudinal alignment with the elongated tubular portion and rotated 360 degrees about the longitudinal axis of the elongated tubular portion.

The following description will describe the new rotating and articulating surgical instrument with regard to a specific embodiment therein of a multiple clip applier. However, it should be understood that the principles involved in the present invention can be applied in whole or in part to various types of endoscopic instruments.

DETAILED DESCRIPTION OF THE DRAWINGS

Referring to the drawings, FIG. 1 is a perspective view of one embodiment of an endoscopic instrument of the present invention;

FIG. 2 is a side view of the instrument shown in FIG. 1 before the trigger is actuated;

FIG. 3 is a side view of the instrument shown in FIG. 1 on actuation of the trigger;

FIG. 4 is a perspective view of the instrument shown in FIG. 1 with the instrument positioned in the cannula of the trocar;

FIG. 16 is a top view of a clip storage track;

FIG. 17 is a side view of the clip storage track shown in FIG. 16;

FIG. 20 is a top view of a feed bar used in instruments of the present invention.

FIG. 21 is a side view of the feed bar depicted in FIG. 20.

FIG. 22 is a top view of a mechanism for actuating the jaws of a surgical clip applier.

FIG. 23 is a side view of the mechanism depicted in FIG. 22.

DETAILED DESCRIPTION OF THE INVENTION

Figure 5:
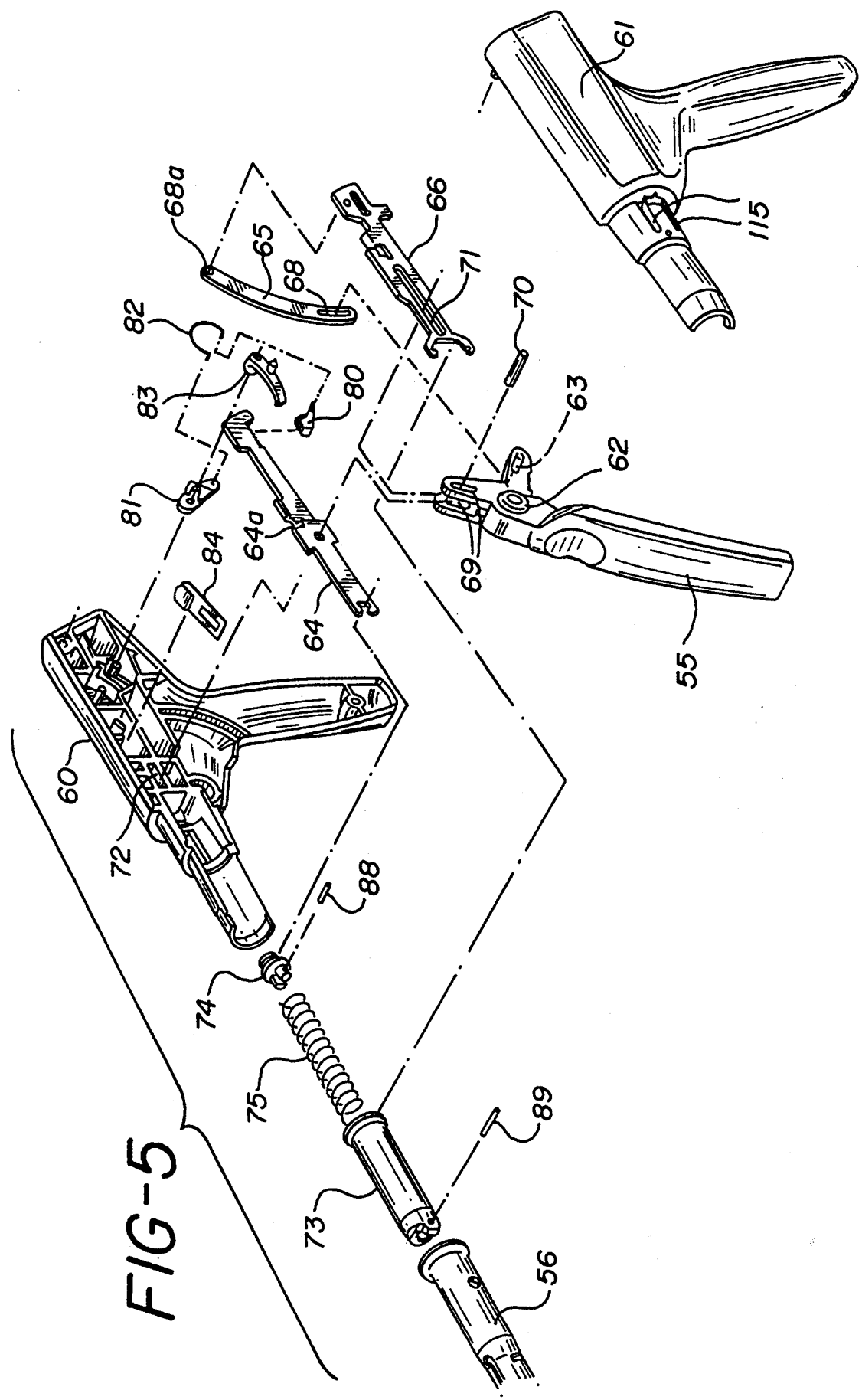
FIG. 5 is an exploded perspective view of a handle of an instrument of the present invention showing various actuating mechanisms.

Referring to the drawings, there is shown an endoscopic rotatable and articulating multiple ligating clip applier 50. As better seen in FIGS. 1-4, the multiple ligating clip applier is useful in applying clips through a surgical trocar. As seen in FIG. 4, the multiple clip applier 50 is applied through the cannula 51 of a trocar 52 so that a ligating clip may be applied to a vessel within the surgical site. The mechanism applies a series of clips 53 by means of jaws 54 which are fired remotely by a trigger 55. As seen in FIGS. 2 and 3, the trigger is compressed causing the jaws to close and squeeze a ligating clip therein. After closing the clip, the jaws are released and another clip is located in place.

Figure 9:
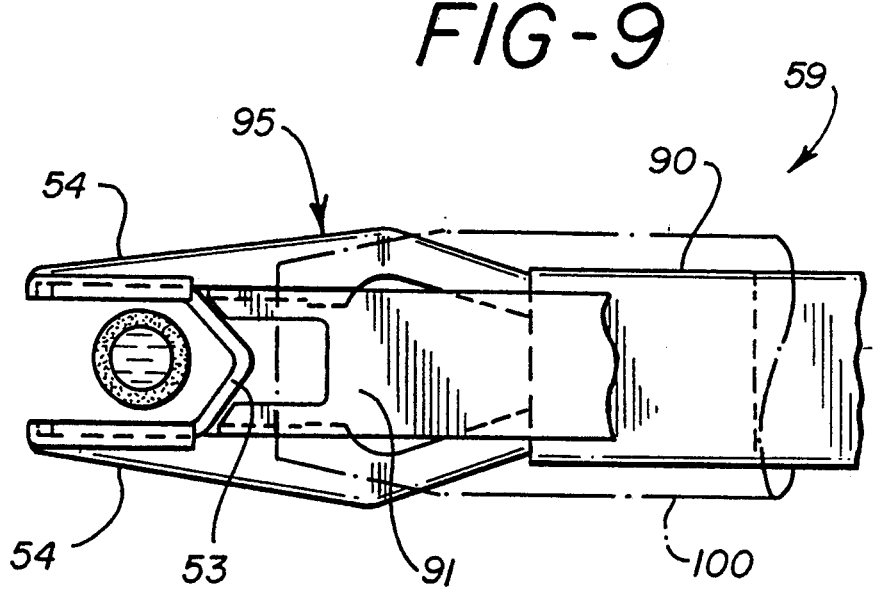
FIG. 9 is an enlarged cross-sectional view of clip applying jaws before the jaws of the instrument have been closed.

As seen in FIGS. 4 and 9, the clip applier presents a pair of jaws 54 which are maintained in a smooth and streamline profile around the ligating clip 53. The jaws fit around a ligating clip so they are relatively the same dimensional width as the diameter of the barrel which forms the support tube 56 of the clip applier. Also a shown in FIGS. 1-3, the multiple clip applier jaws and support tube are rotatable and the clip applying end 59 of the instrument may be articulated up to 45° or even more from its longitudinal axis. The support tube and clip applying end of the instrument may be rotated 360° about its longitudinal axis utilizing the rotating knob 57. Also the very end; that is, the clip applying end of the instrument may be articulated or moved out of alignment with the longitudinal axis of the support tube about 45° or more utilizing the articulating knob 58. As can be appreciated, this combination of rotation and articulation allows for considerable flexibility in applying a clip within the surgical environment.

Figure 6:
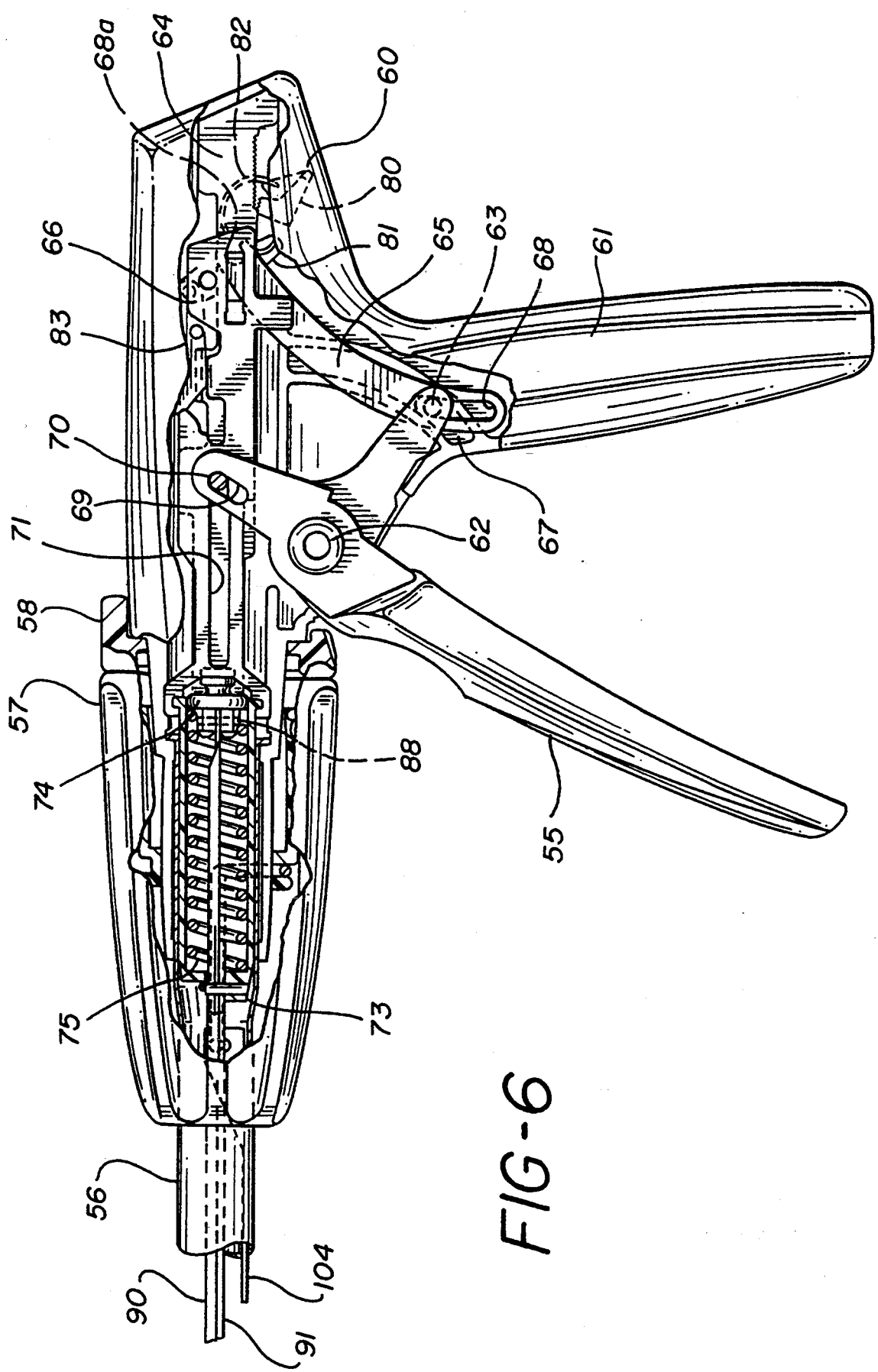
FIG. 6 is a cross-sectional view of the handle mechanism shown in FIG. 5 before the trigger is actuated.
Figure 7:
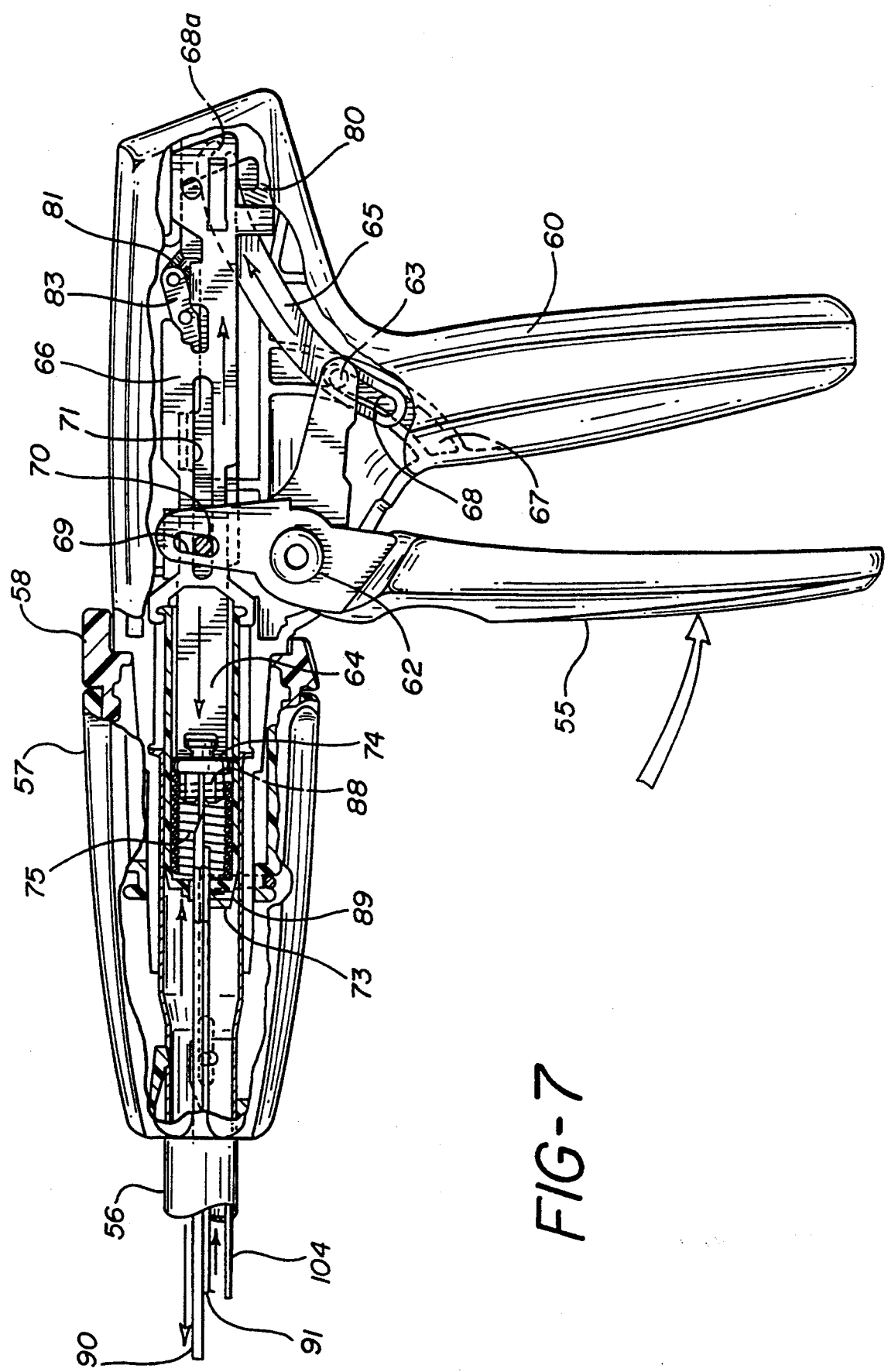
FIG. 7 is a view similar to FIG. 6 on actuation of the trigger.
Figure 8:
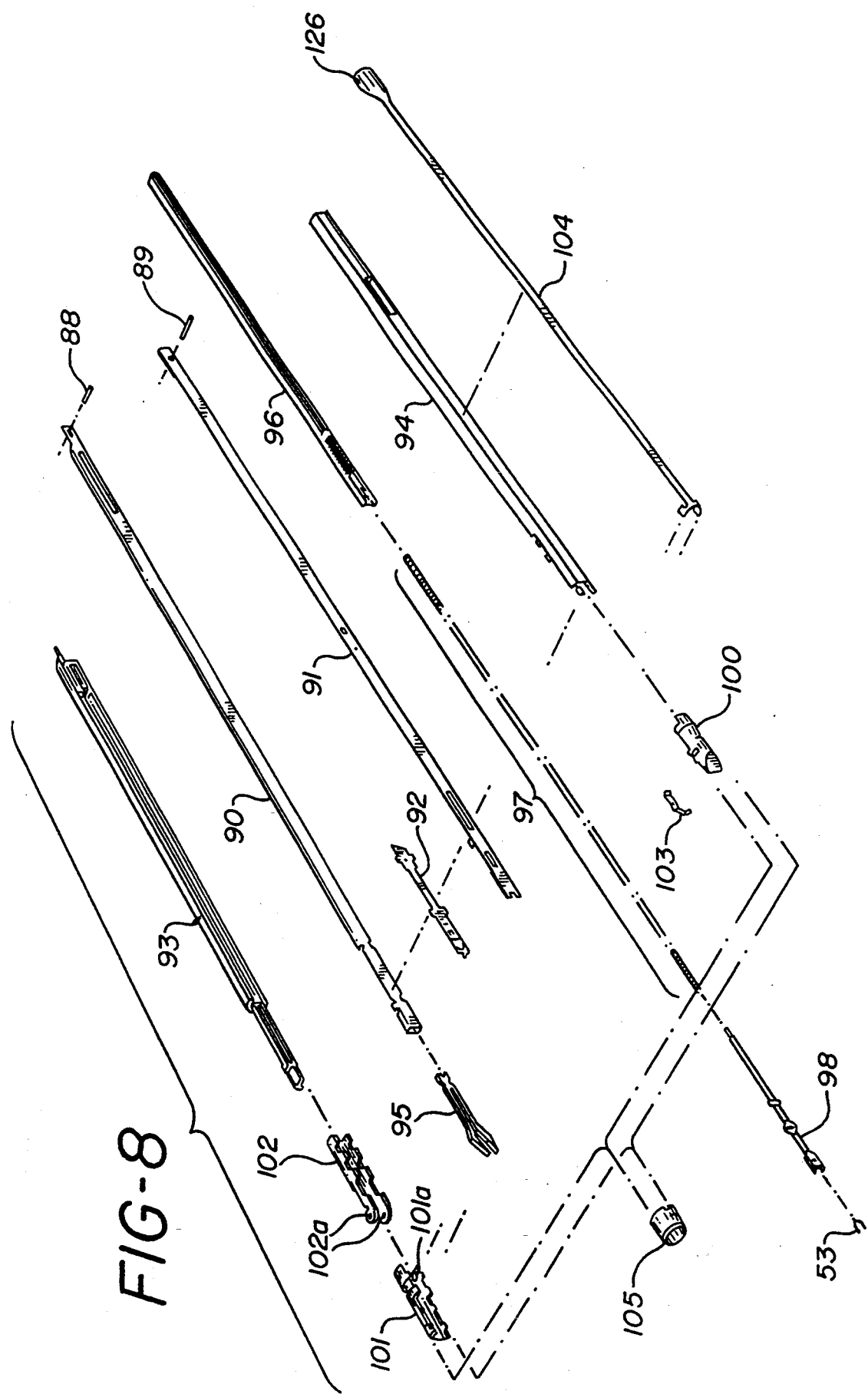
FIG. 8 is an exploded perspective view of the elongated tubular portion and of the articulating head of an instrument of the present invention.

As better seen in FIGS. 5, 6 and 7, there is described handle halves 60 and 61 which enclose the trigger mechanism 62. The handle halves surround the firing mechanism and form a pivot point 63 around which the trigger rotates. The trigger is associated with a former plate 64 and a feeder link 65. The feeder link is attached to the trigger and holds the feeder plate 66 in place, thus, when the trigger is fired, the former plate is pushed forward. Pivot 63 on the trigger slides in the channel 67 in the handle half 60 and causes the slot 68 to be urged towards the rear of the instrument. The slot 68a on the feeder link in turn causes the feeder plate to be urged to the rear of the instrument. Simultaneously, as the trigger rotates the slots 69 cause dowel pin 70 to slide in the slot 71 of the feeder plate. The dowel pin 70 urges the former plate forward as the dowel pin slides within the slot 72 in handle half 60. The former plate is attached to an inner coupling 74 and the feeder plate is attached to an outer coupling 73. As shown in FIG. 8 a cam channel 90 is attached to the inner coupling by connecting pin 88. The feed bar 91 is attached to the outer coupling by connecting pin 88. When the trigger is squeezed the former plate moves forwardly and the inner coupling 74 compresses the spring 75 within the outer coupling 73. The inner and outer couplings are contained within the support tube 56. When the trigger is released, the compression on the spring is released and causes the trigger to return to its original position. This causes the feeder plate and the former plate to return to their non-stressed positions. An anti-backup lever 80, a lost motion lever 81, a torsion spring 82, a prelock trigger 83, and a lock-out latch 84 will all be further described with regard to the multiple clip applier.

As previously mentioned, the feeder plate 66 is attached to the outer coupling 73 and the former plate 64 is attached to the inner coupling 74. The inner coupling slides or moves longitudinally within the outer coupling. A compression spring 75 is disposed in the outer coupling as shown. When the trigger is activated, the feeder plate moves rearwardly and pulls the outer coupling rearwardly compressing the spring. Simultaneously, the inner coupling attached to the former plate moves forwardly also compressing the spring. The geometry of the mechanism allows the outer coupling to move rearwardly at a faster rate initially to allow the feed bar 91 to clear the jaws of the instrument before the jaws are closed in response to the forward movement of the former plate. Also, the shape of the slot 69 in the trigger 62 will provide time for the feed bar to clear the jaws before the jaws are closed. If it is desired to increase the time for the feed bar to clear the jaws, a further semi-circular cutout may be placed in the slot to provide dwell time for the pivot pin 70 and delay the jaws closing. Once the feed bar has cleared the jaws, the rate of rearward motion of the feeder plate is appropriately reduced.

As seen in FIG. 8, the feed bar 91 and cam channel 90 surround a floor 92. These mechanisms are slidably encased between a lower spacer 93 and a top spacer 94 all of which are disposed within the support tube. Attached to the cam channel is jaw mechanism 95. This jaw mechanism will close about a ligating clip 96.

Disposed between the feed bar and top spacer is the clip track 96. Disposed in the clip track is a feeder spring 97, a feeder shoe 98, and a series of clips. The clip track is capable of advancing forward a series of clips and loading them within the jaws. Extending from the top and lower spacers is the articulating portion of the instrument. This portion comprises a top shroud 100 and a lower shroud 101. The lower shroud is hingedly connected to hinge 102 by the pivot pins 101a. The hinge 102 is attached to the lower spacer 93. The top shroud 100 is attached by a snap fit to the lower shroud.

A lifter spring 103 is held in place over the clip track by the top shroud and places the first clip from the stack of clips in the plane of the feed bar to be fed to the jaws.

In order to articulate the jaws or the business end of the instrument, an articulating strap 104 is connected to the shrouds by the retaining sleeve 105. The opposite end of the articulating strap is connected to the articulating knob as will be hereinafter described.

It is preferred that the attachment of the articulating strap to the articulating portion of the instrument be made distally of the pivot point 102a. Such an attachment provides greater ease in articulating the head of the instrument.

Figure 10:
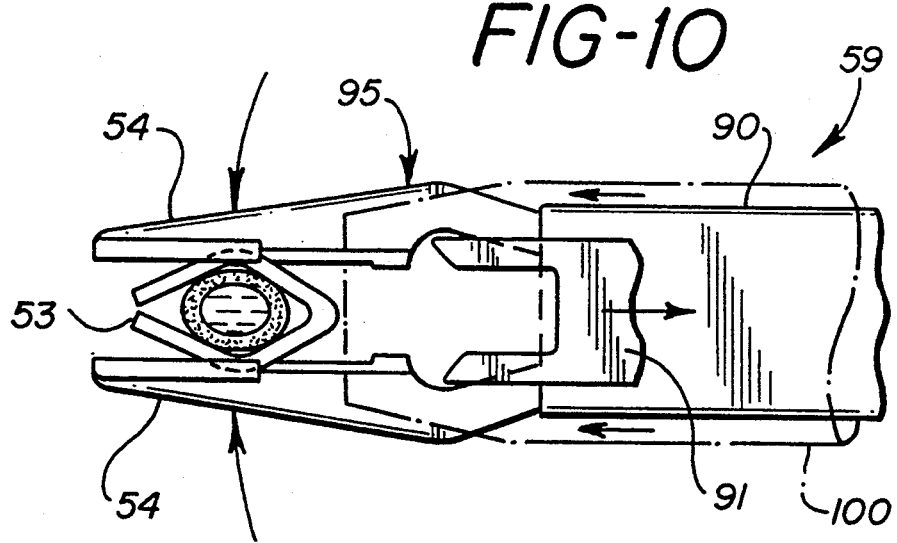
FIG. 10 is an enlarged cross-sectional view similar to FIG. 9 on partial closing of the clip applying jaws.
Figure 11:
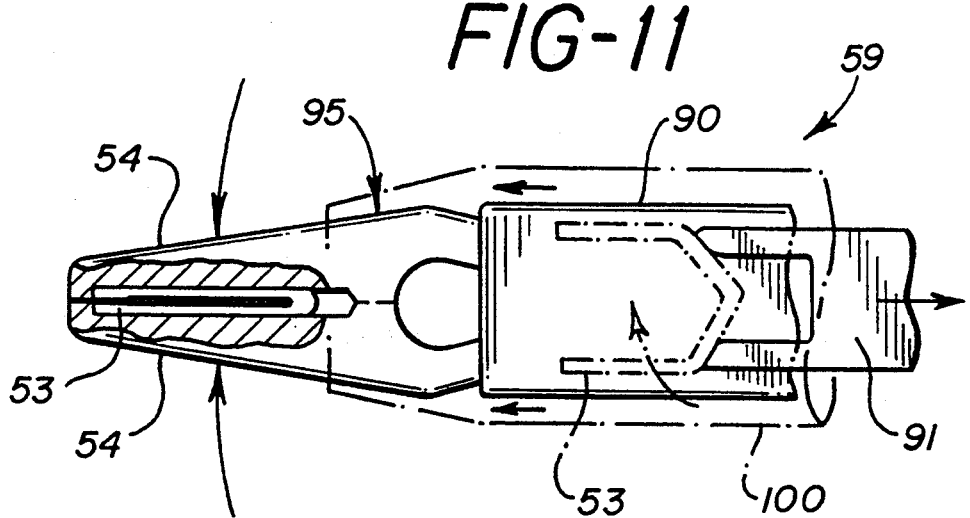
FIG. 11 is an enlarged cross-sectional view similar to FIG. 9 on the closing of the clip applying jaws.

In operation, the former plate causes the cam channel to move forward. The cam channel causes the jaws to close and place a clip around tissue or a vessel. When the trigger is released, the cam channel retracts and the jaws open. The magazine of clips is advanced forward so that another clip may be fed to the jaws. This occurs when spring 75 is allowed to return to its uncompressed position causing the feeder plate to move forward. This, in turn, causes the feed bar to advance the first clip from the stack of clips into the jaws. This operation can best be seen by observing FIGS. 9, 10, and 11 in connection with FIGS. 6 and 7.

A feature that may be incorporated in the instrument of the present invention is a clip closure cam channel such as that described in co-pending commonly assigned patent application Ser. Nos. 822,478 and 680,215, (now U.S. Pat. No. 5,171,249) which is incorporated, in its entirety, herein by reference. A lost motion lever 81, an anti-back up lever 80, a torsion spring 82 and a pre-clock trigger mechanism 83 all described in said co-pending application may also be incorporated in the instrument of the present invention. Also, if desired, appropriate sealing, filtering, or restriction means may be incorporated in the instrument of the present invention as is well-known in the art.

Referring to FIG. 5, there is shown a last clip lock out latch 84. This latch will prevent the trigger from being squeezed after the last clip has been placed. This provides the surgeon with the information that there are no more clips in the instrument. When the last clip has been placed and there are no more clips in the instrument, the feed bar end of the feed plate does not move as far forward as usual with clips remaining. This allows the latch 84 to drop down into the catch 66a on top of the former plate and prevent any further actuation of the instrument.

Figure 12:
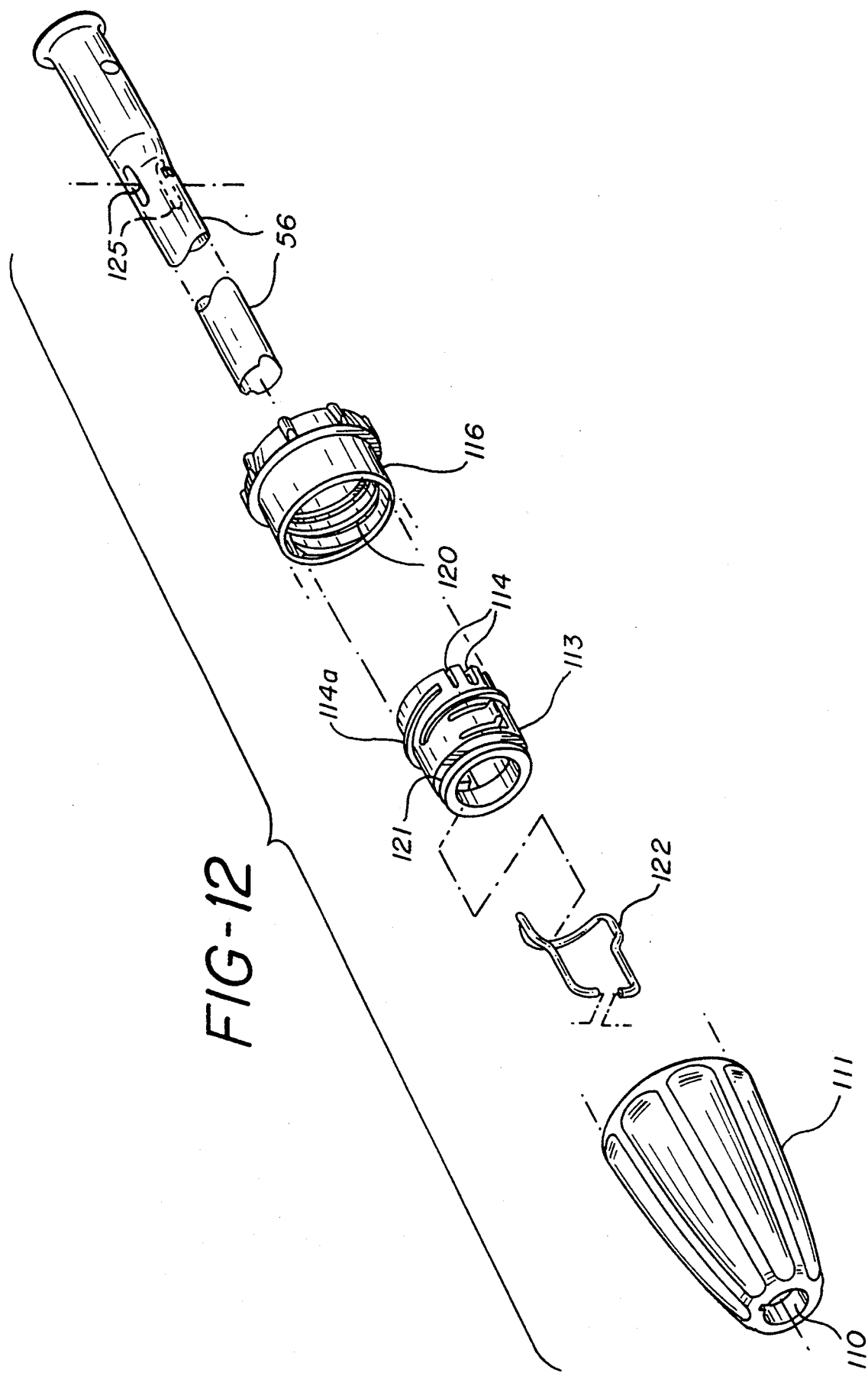
FIG. 12 is an exploded perspective view of a rotational mechanism and a portion of the articulating actuating means used in instruments of the present invention.
Figure 13:
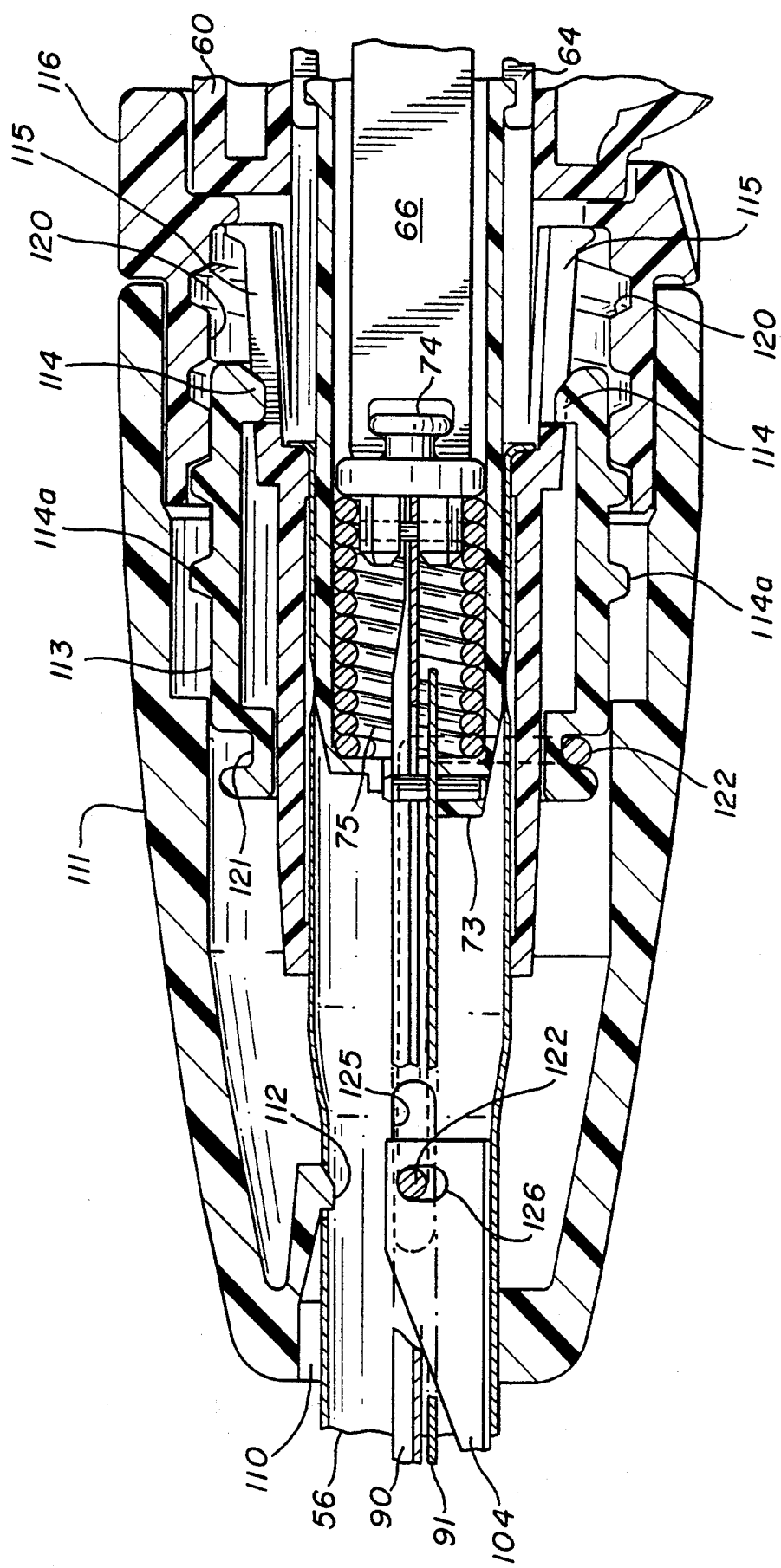
FIG. 13 is a cross-sectional view of the mechanism depicted in FIG. 12.

The rotation mechanism and the articulation mechanism of the present invention are more clearly shown in FIGS. 12 and 13. The support tube 56 fits through an opening 110 in a rotation knob 111. The rotation knob includes a tab 112 which fits into an indent or opening in the support tube as shown. When the rotation knob is turned, the support tube, the mechanism contained within the support tube and the outer coupling rotate with the rotation of the knob. The cam channel, floor, feed bar, etc., all rotate with the support tube. Also mounted on the handle between the rotation knob and the trigger portion of the handle is the articulation mechanism. This mechanism comprises a longitudinally movable member 113 which has a male thread 114 on its outer surface. The member has tabs 114a which engage the longitudinal slots 115 in the handle halves. By being fixed in the slots, the member is prevented from rotating but can move longitudinally back and forth in the slots 115. A second member 116 also fits over the handle but is allowed to rotate with respect to both the handle and the support tube. This member includes a threaded section 120 which interengages with the threaded section on the longitudinally movable member 113. Hence, when the member 116 is rotated, it will cause the longitudinally movable member to move back and forth longitudinally along the axis of the support member. At the distal end of the longitudinal member is a groove 121 and disposed in this groove is a wire 122 which is movable circumferentially in the groove. The ends of the wire are disposed through the longitudinal slots 125 in the support tube. The ends are then affixed in the holes 126 in the proximal end of the articulation strap. Hence, when the rotational knob rotates the support tube and clip applying mechanism of the device, the wire spring also rotates about the articulation member 113 and maintains proper alignment. Once the clip applying mechanism is in a desired rotational position, the articulation knob may be rotated to move the longitudinally movable member along to the longitudinal axis and move the articulation strap parallel to the longitudinal axis of the instrument articulating the clip applying head of the instrument.

Figure 14:
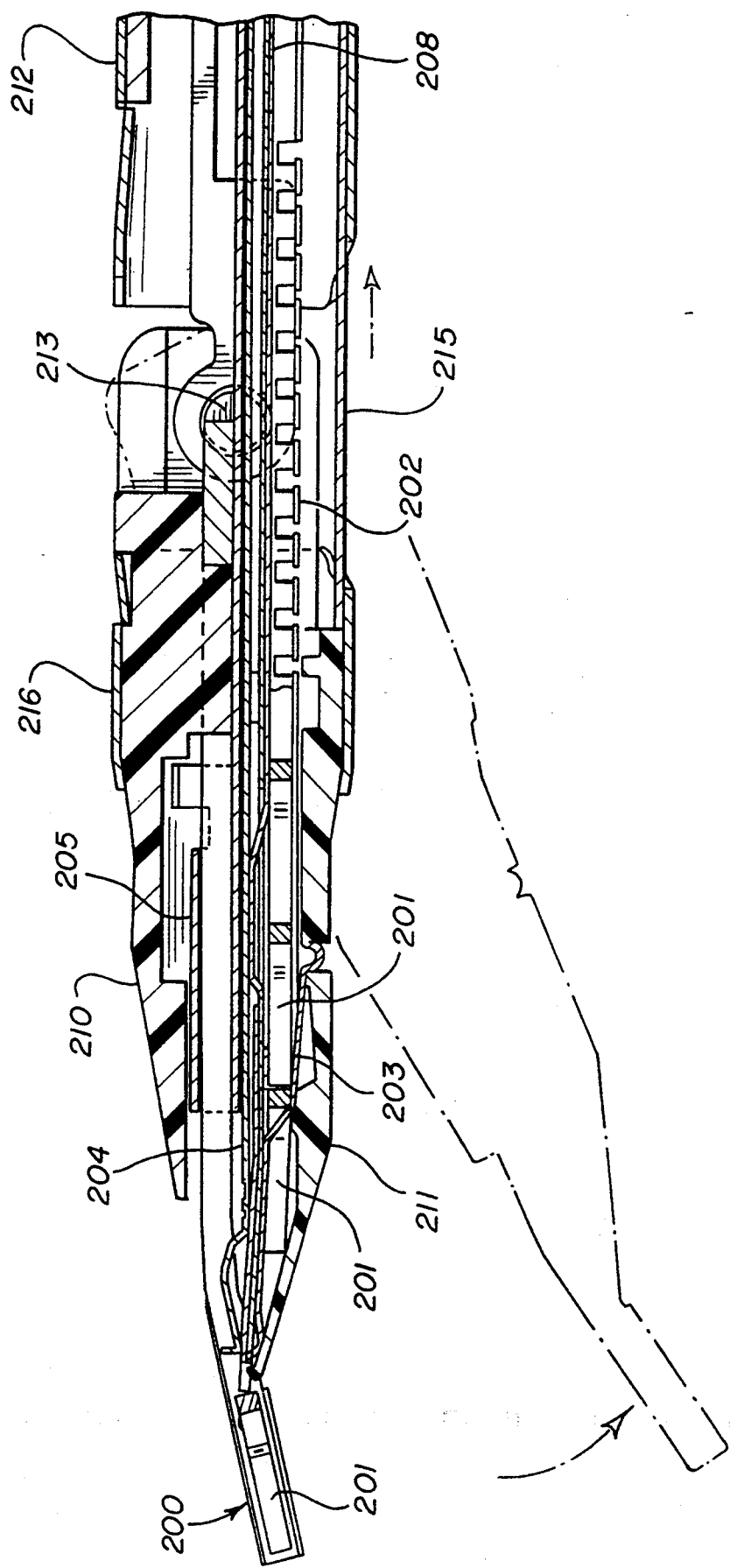
FIG. 14 is an enlarged cross-sectional view of a fastener head of an instrument with a clip in the jaws ready to be applied.
Figure 15:
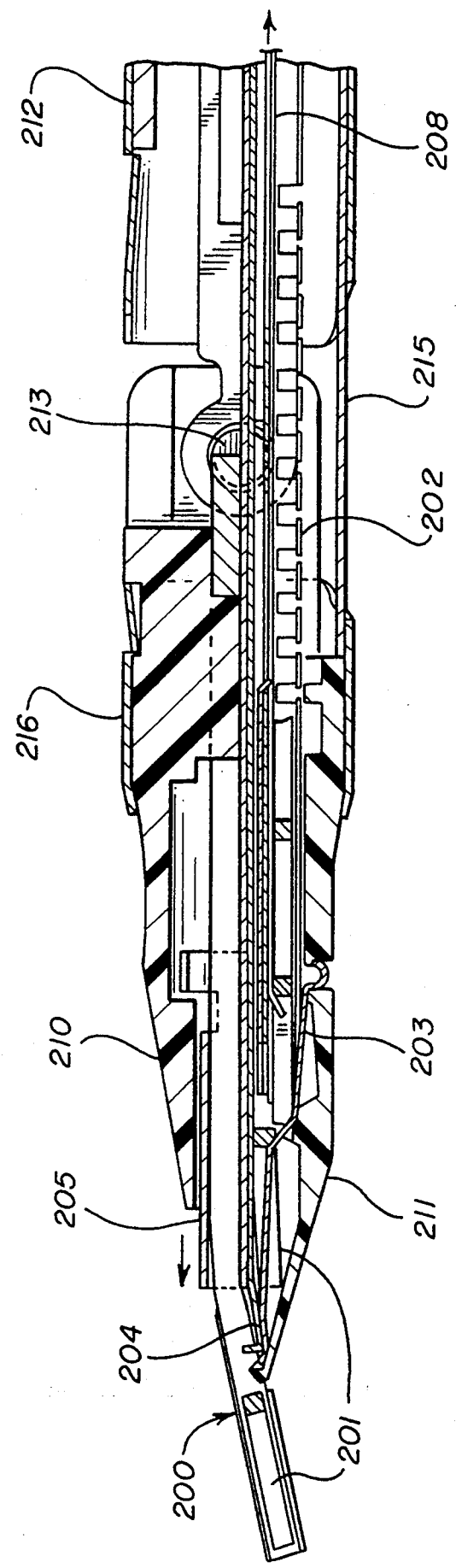
FIG. 15 is a view similar to FIG. 14 after the jaws have been closed.
Figure 29:
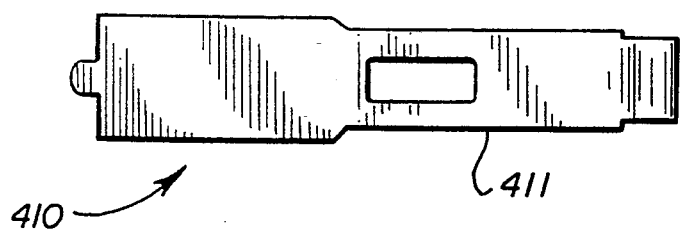
FIG. 29 is a top view of a lifter spring used in the instrument of the present invention.
Figure 30:
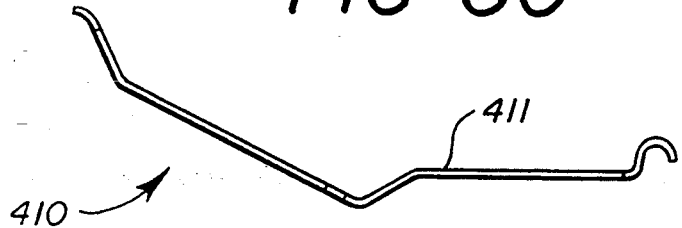
FIG. 30 is a side view of the lifter spring depicted in FIG. 29.

The operation of the clip applying mechanism; that is the closing of the clips by the jaws of the instrument as well as the feeding of the clips to the jaws, will be more fully described in conjunction with FIGS. 14 and 15. FIGS. 14 and 15 are enlarged cross-sectional views of the business end or front portion of the instrument. In FIG. 14, the jaws 200 are in an open position with clip 201 positioned in the jaws. In FIG. 15, the jaws are in a closed position, A series of clips are held in a deflectable clip track 202. The clips are held in the track and continuously biased forwardly by the feeder spring and feeder shoe described in conjunction with FIG. 8. Positioned below the clip track is a flexible feed bar 208. When the feed bar is moved to its rearward most position as shown in FIG. 15, a lifter spring 203 pushes the next clip in front of the feed bar. When the jaws are closed, to close a clip, and then allowed to open the feed bar moves forwardly pushing the next clip into the jaws. The lifter spring also acts as a lock-out mechanism. As shown in FIGS. 29 and 30, the lifter spring 410 has a reduced down portion 411. If there is a clip in front of the clip track, it will keep the lifter spring elevated as seen in FIG. 14. After the last clip has been placed in the jaws and the jaws closed, the lifter spring is permitted to move in front of the feed bar. The lifter spring engages the fork at the front of the feed bar and locks the feed bar and the lock latch and the handle locks the fomer plate and dowel pin and, hence, the trigger.

Mounted under the feed bar is the floor 204 and on under the floor is the cam channel 205. When the jaws of the instrument are open, the cam channel is in its rearward most position. In operation, when the feed bar goes back towards the handle, a clip rides up and is placed in front of the feed bar. The cam channel moves forwardly and the feed bar goes rearwardly simultaneously. The feed bar goes back at a faster rate at first so that it clears out of the way of the closing jaws. The cam channel, the feed bar, the floor and the clip track are all flexible and are contained within the articulatable shroud head. The pair of shroud members 210 and 211 extend from the support tube 212. The lower shroud 210 is pivotally connected to the support tube by pivot pins 213. An articulation strap 215 extends from the proximal end of the support tube to the upper shroud 211. The shrouds snap together and the articulation strap and the shrouds are held together by retaining sleeve 216. This provides attachment of the strap distally of the pivot pin 213. As previously described, as the articulation knob is turned, tension is placed on the articulation strap to move it so that it is urged toward the rear of the instrument. This action causes the two shrouds as well as the clip applying jaws and those portions of the clip track, feed bar, floor, cam channel, etc. within the shrouds to bend or articulate about the articulation pivot pins, or actually, more or less, float in the center of the articulation area.

The articulation of the head of an endoscopic instrument in many instances poses a number of problems. For example, the forces required to articulate the head of the instrument increase as the degree of articulation is increased. Because the force to articulate is applied a substantial distance away from the articulating head, the forces required may be considerable. In an endoscopic procedure, it is desirable to keep the forces that a surgeon is required to use in order to manipulate a surgical instrument to a minimum. One method of reducing the forces required to articulate the head of the instrument is to pre-bend some of the articulating parts a fraction of the total degree of articulation. For example, in the clip applier described which has a maximum degree of articulation of 45 degrees, it may be desirable to pre-bend the cam channel, feed plate, clip track and/or floor 22.5 degrees. The pre-bend should occur at the area of each of the members that passes through the pivot point of the articulating head. Also, many of the instruments require a number of mechanical devices to perform an operation or series of operations such as a multiple clip applier. Those devices must operate smoothly and reliably along the various radii of articulation. Furthermore, the mechanical devices must maintain their relative motions and performance with respect to each other at the various radii of articulation. The following mechanisms overcome these problems.

Figure 18:
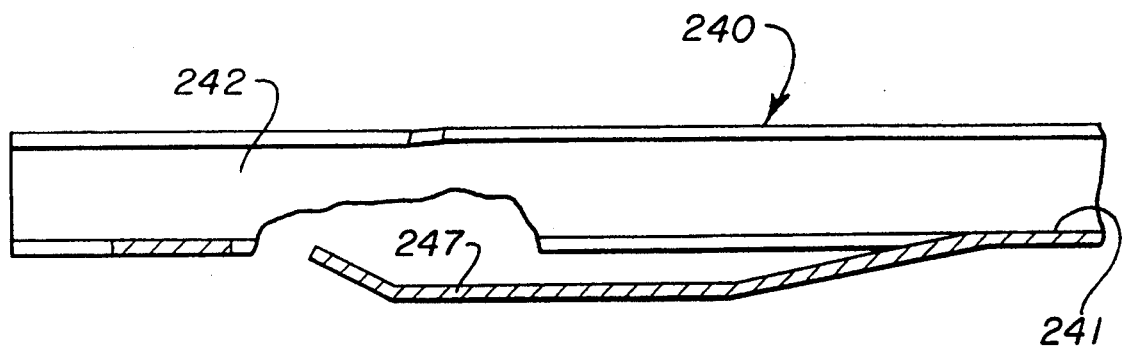
FIG. 18 is an enlarged side view of the front portion of the clip storage track.
Figure 19:
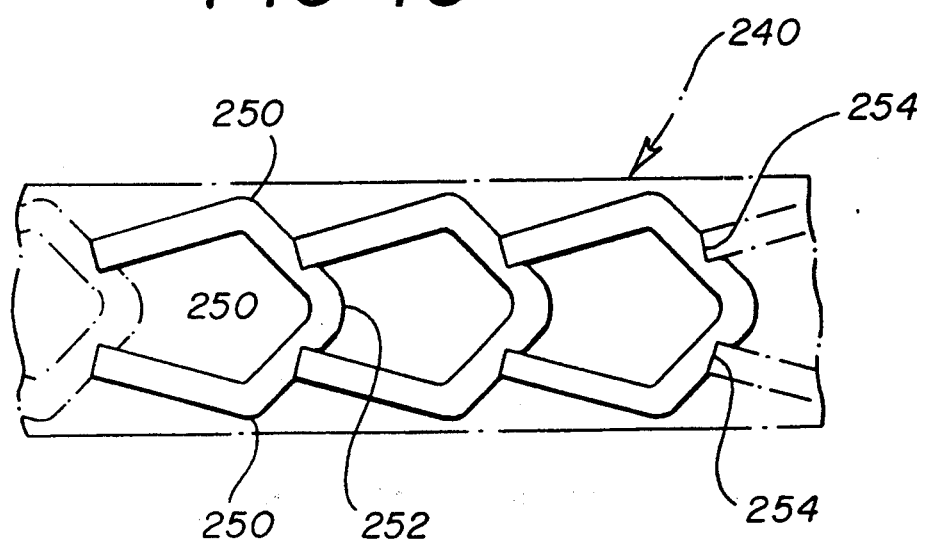
FIG. 19 is a schematic view of clips as they would appear in a clip storage track.

Referring to FIGS. 16, 17 and 18, there is depicted a flexible clip track used in the instrument of the present invention. The clip track 240 is a channel having a bottom floor 241 and upwardly standing lateral walls 242 and 243. There is an inwardly extending flange portion 244 and 245 from the top of each side wall. Disposed in the channel are a plurality of clips. The clips are continuously biased forwardly to the open end of the clip track by a compression spring which is compressed against the closed end of the channel and is held or guided in place by the flexible feed shoe 98, as previously described in conjunction with FIG. 8. The flexible portion of the clip track, which is the portion that articulates or flexes in the articulating end of the instrument has openings 246 in the side walls. The openings are relatively narrow adjacent the overhanging upper portion of the track but are expanded, as shown in FIG. 17, in the lateral side of the track. This allows this portion of the track to bend or flex as the head of the instrument is being articulated. The larger the openings 246 in the side walls, the greater the flexibility of the track but the less the clip entrapment within the track. The narrowed portion along with the overhanging flanges provides the necessary clip entrapment. The narrow area at the top of the cutout defines the minimum allowable radius the track may be bent without pinching the clips as they move along the track. Also, the bottom floor of the track in the area of the openings is also open to allow the clips to ride smoothly around any bending of the track and not bind on the floor of the track. The structure of the track as described above allows a substantial number of clips to be stored in both the articulating portion and the non-articulating portion of the track while allowing those clips to be smoothly and reliably fed to the articulating jaws of the instrument. The flexible feed shoe will pass through the articulating section to allow all of the clips stored in the instrument to be fed to the jaws. An enlarged view of a series of clips is shown in FIG. 19. As seen, each clip comprises a pair of legs 250 connected at one end of the legs by an arcuate section 251. As seen, the apex 252 of each clip is disposed between the legs of the adjacent clip. As can be appreciated, when moving these clips around a bend, the apex of the clip will fall out of line or out of the general plane of the clips. To accommodate this, the clip track has an open section in the bottom floor of the track in that area where it is flexible as previously described. This allows the apex of the clip as it goes around a bend not to be held up by the clip track. In feeding clips around a radius, it is possible that the tips of the legs of the clip may be snagged on the mechanism encasing the clips and reduce the reliability of clip feed in the instrument. This problem is solved by insuring that the tips of the legs of the clips are always narrower than the knees 253 of the clip and it is the knees of the clip that ride on the side members of the clip track. Also, the arcuate connecting portion of the clip may include a pair of dimples 254 in which the legs of the following clip reside and aid in holding the line of clips in the desired position throughout the feeding of the clips. At the front of the clip track, there is a cutout deflectable portion 247 as shown in FIG. 18. The function of this portion is to hold the clips in place and release them at the appropriate time. This deflectable portion is pressed down at the appropriate time so that its leading edge engages the arcuate portion of a forward most clip in the clip track to prevent it from being biased into the jaws of the instrument at the incorrect time as will be more fully explained in conjunction with the feed bar. Also, at the front portion of the clip track, immediately in front of the cut-out portions, there are a pair of upwardly extending tabs 248. These tabs are used to reference the clip track to the other moving parts of the instrument within the articulation head as will be described hereinafter.

Referring to FIGS. 20 and 21, there is shown the feed bar 260. The feed bar is a thin metal strip preferably of spring steel or other similar flexible material. The strip has a double thickness at its distal end 261 to provide rigidity. The bar may also include an upstanding ridge 262 over a portion of its length to provide rigidity to the bar in the rigid portion of the endoscopic section of the instrument. The proximal end of the feed bar is connected to the trigger mechanism, as previously described, so that as the clips are closed the feed bar moves rearwardly out of the way of the closing jaws and allows another clip to be positioned in front of the feed bar. When the jaws are allowed to open the feed bar moves forwardly feeding another clip into the jaws. The feed bar has openings 263 and 264 in its surface to improve flexibility. Also, the forward or distal opening 263 allows the deflectable portion 247 of the clip track (shown in FIG. 18) to deflect into the opening and allow another clip to be released from the clip track. The feed bar also includes a pair of upstanding tabs 265 which are used to reference the feed bar in the articulating head as will be hereinafter described.

Another moving part in the articulating head is the flexible cam channel 270 which will be more fully described in conjunction with FIGS. 22 and 23. The channel comprises a bottom or floor 271 and a pair of side members 272 and 273 extending upwardly from the outer edges of the bottom or floor.

Figure 24:
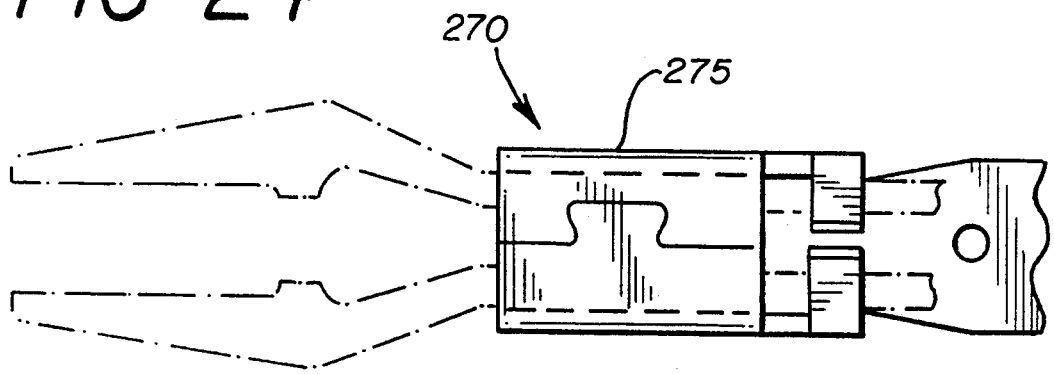
FIG. 24 is a schematic side view of a means for closing clip applying jaws.
Figure 27:
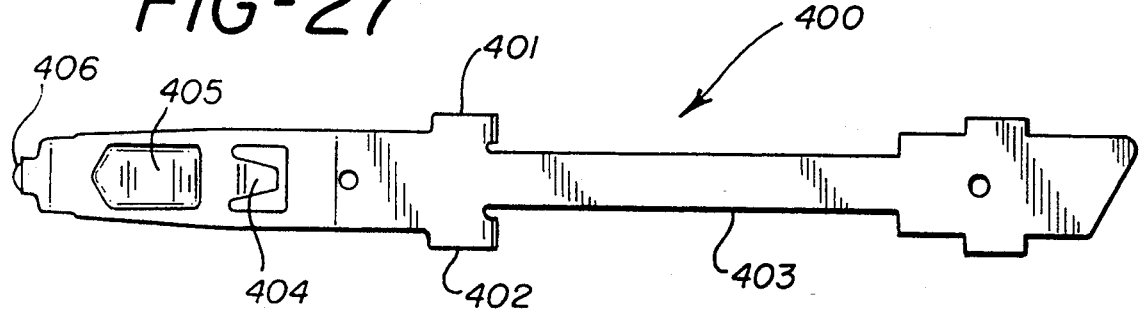
FIG. 27 is a top view of a floor used in instruments of the present invention.
Figure 28:
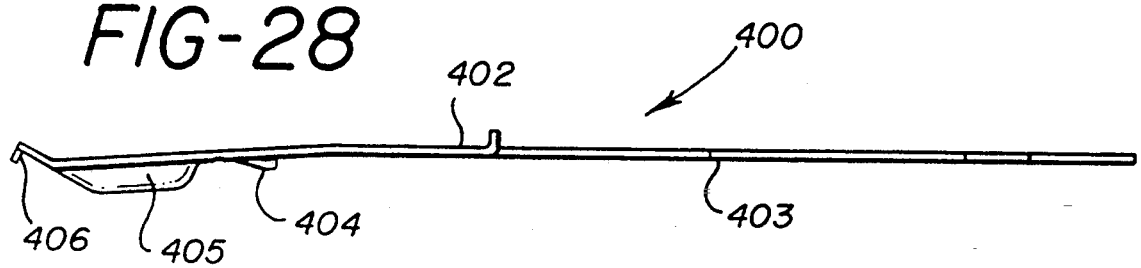
FIG. 28 is a side view of the floor depicted in FIG. 27.

The cam channel is preferably made of spring steel. The side members extend from the proximal end where the channel is connected to the inner coupling as previously described, to a thinned flexible area having no side members. The side members provide some rigidity to the channel while the thin area allows the channel to flex in the articulating portion of the instrument. The distal end 275 of the channel is enclosed to form an opening in which the jaw mechanism of the instrument is held. This is more clearly shown in FIG. 24. As the channel moves forward, it meets the diverging outer surfaces of the jaws to close the distal portion of the jaws. When the channel moves rearwardly, the jaws are allowed to open to receive the next clip. The cam channel also has a pair of upstanding tabs 276 at the distal end of the channel to reference the channel to the other moving parts in the articulation head as will be hereinafter described. Positioned between the cam channel and the feed bar is the floor. FIG. 27 is a plan view of the floor and FIG. 28 a side elevation of the floor. The floor 400 is generally rectangular in shape. The floor has two outwardly extending tabs 401 and 402. The tabs are used to position the floor correctly in the lower shroud. Adjacent and proximal of the tabs is a narrow section 403. The tabs on the feed bar are positioned on each side of the narrowed section. Immediately adjacent the tabs and distal thereof is a deflectable portion 404. The distal end of the floor has a scoop 405 and an upstanding end 406. The upstanding end is positioned behind a clip in the jaws to prevent backward motion of the clip as the jaws are closed and applied. When the feed bar retracts, it presses the deflectable portion and moves the upstanding end out of the path of the next clip to be fed to the jaws. The scoop area allows the next clip to be rotated and placed in the jaws.

Figure 25:
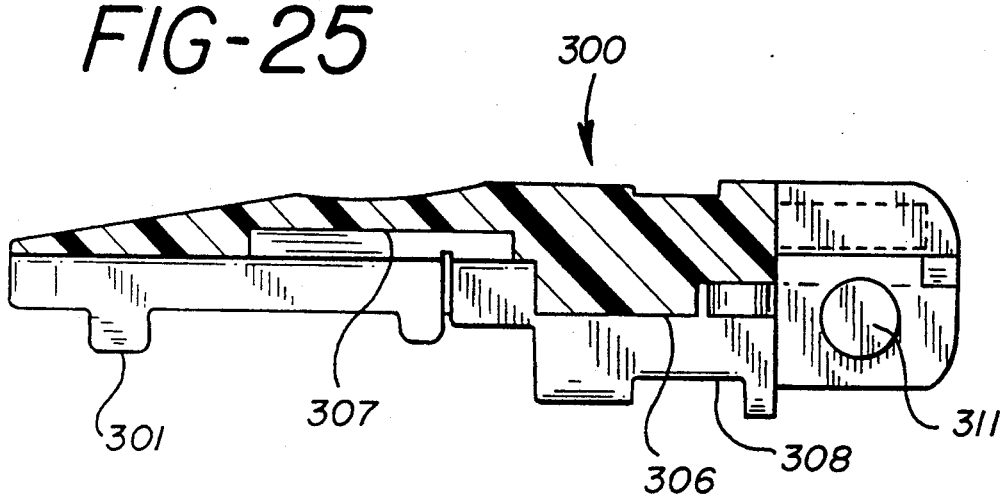
FIG. 25 is a cross-sectional view of a portion of a fastener applying head useful in the instrument of the present invention.
Figure 26:
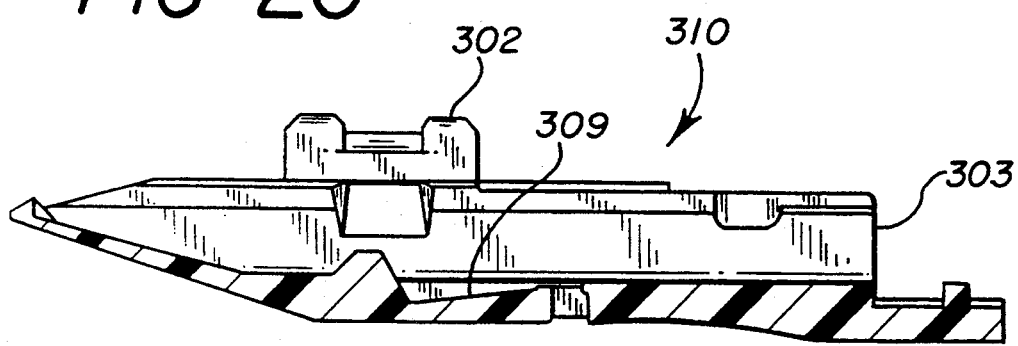
FIG. 26 is a cross-sectional view of another portion of the fastener applying head.

As previously mentioned, it is extremely important in an articulating instrument that all the moving parts be referenced to the instrument so that the relative motion between the parts remains substantially the same throughout all degrees of articulation. The moving parts should be referenced to the articulating head or business end of the instrument so their position with respect to the head remains the same through all degrees of articulation. This is accomplished by indexing the various movable parts with respect to each other and to the head of the instrument. This will be more fully described in conjunction with FIGS. 25 and 26. The articulating head of the instrument comprises a lower shroud 300 (FIG. 25) and a top shroud 310 (FIG. 26) which encase the moving parts. The lower shroud 300 is pivotally connected to a member which is held by the support tube as previously described in conjunction with FIG. 8. The lower shroud has a pair of tabs 301 and the upper shroud has a pair of cooperating tabs 302 which snap fit together to hold the two shrouds together so that the back end 303 of the top shroud is adjacent the wall 304 of the lower shroud. Between these shrouds there are disposed the cam channel, the floor, the feed bar, and the clip track carrier. Also, the jaws are disposed in the cam channel as previously described. Fitting about the shrouds in a groove is the articulation strap which is connected back to the articulating knob as previously described. The articulation strap and the shrouds are held together by a retaining sleeve The jaws are held in place by the tear drop projection 306 disposed on the lower shroud. This tear drop projection fits into the opening immediately behind the legs of the jaws and acts as the reference point for the moving parts. As shown in FIG. 25, the lower shroud 300 has a trench 307 in its bottom surface. The tabs on the cam channel (shown in FIG. 23) slidably engage the trench and define the limits of movement of the cam channel. The side tabs of the floor (shown in FIG. 27) sit in the indentation 308 in the lower shroud. The upstanding tabs of the feed bar (shown in FIG. 23) move along the outside of the narrowed section of the floor (shown in FIG. 27). The top shroud also has a narrow trench 309 in its bottom surface. The reference tabs of the clip track (shown in FIG. 17) slidably engage the trench and define the proximal and distal limits of the movement of the clip track. The retaining sleeve locks the shroud together and insures that the moving parts between the shrouds are properly referenced with respect to each other and to the jaws at any radius of articulation.

The clip track, feed bar, floor and cam channel all are referenced either directly or indirectly to the same point.

It should now be evident that there is described herein an improved endoscopic instrument that provides a high degree of accessibility and mobility. Although the invention has been described by way of examples of preferred embodiments, it will be evident that other adaptations and modifications may be employed without departing from the spirit and scope of the invention.

What is claimed is:

1. A rotatable, articulating, endoscopic multiple clip applier for applying a plurality of clips in seriatim to body tissue comprising, an elongated hollow shaft assembly having a hingedly attached distal end portion, said assembly containing a jaw member having a pair of spaced apart jaws for receiving a surgical clip therebetween, a clip storage and placement mechanism for storing an array of clips and placing the distal most clip of said array in a position to be fed between said jaws, a clip feed member for feeding said distal most clip to said jaws, a jaw closure mechanism for contacting said jaws and closing a clip positioned between said jaws, and an articulating mechanism attached to said distal end portion for moving said distal end portion of said elongated hollow shaft assembly in and out of longitudinal alignment with the rest of said elongated hollow shaft assembly;

a handle assembly rotatably connected to said shaft assembly containing means for actuating said jaws and for actuating said clip feed member;

a rotating assembly attached to said elongated hollow shaft assembly to rotate said assembly about its longitudinal axis; and an articulating knob for actuating the articulating mechanism to move the hingedly attached distal end portion of said elongated hollow shaft assembly in and out of longitudinal alignment with the rest of said elongated hollow shaft assembly.

2. A rotatable, articulating endoscopic multiple clip applier according to claim 1 wherein said distal end portion is pivotally attached to said elongated hollow shaft assembly.

3. A rotatable articulating endoscopic multiple clip applier according to claim 1 wherein the clip storage and placement mechanism, the clip feed member and the jaw closure mechanism are all flexible in the area where the distal end portion is hingedly attached to the elongated shaft assembly.

4. A rotatable, articulating, endoscopic multiple clip applier according to claim 1 wherein the clip storage and placement mechanism is a member having a rectangular cross-section defining a floor, lateral side walls, and a top overlying a portion of the clips, said lateral side walls having spaced apart openings disposed therein in that portion of the mechanism on both sides of the hinged attachment of the distal end portion to the rest of the elongated hollow shaft assembly.

5. A rotatable, articulating endoscopic multiple clip applier according to claim 4 wherein the openings in the lateral side wall extend into the top of the clip storage and placement mechanism and the portion of the openings in the top are narrower than the portion of the openings in the lateral side wall and the floor of the clip storage and placement mechanism has an opening therein in that portion of the floor wherein there are openings in the lateral side walls.

6. A rotatable, articulating endoscopic multiple clip applier according to claim 5 wherein the hingedly attached distal end portion is pivotally attached and the strap member is attached to the distal end portion distally of said pivotal attachment.

7. A rotatable, articulating endoscopic multiple clip applier according to claim 1 wherein the articulating mechanism is a strap member extending from the hingedly attached end portion to the articulating knob and said articulating knob includes means to allow said strap member to rotate with the rotating assembly.

8. A rotatable, articulating endoscopic multiple clip applier according to claim a wherein the hingedly attached distal end portion includes means for maintaining the relative positions of the clip storage and placement mechanism, the clip feed member and the jaw closure mechanism throughout articulation of the distal end portion.

9. A rotatable, articulating endoscopic multiple clip applier according to claim 1 wherein the handle assembly includes a single trigger means for actuating the jaw closure mechanism to close a clip positioned in said jaws and for actuating said clip feed member to deliver a clip to said jaws.

10. A rotatable, articulating endoscopic multiple clip applier according to claim 1 wherein the distal end portion is pivotally attached to the rest of the elongated hollow shaft assembly, the clip storage and placement mechanism is a member having a rectangular cross-section defining a floor, lateral side walls, and a top overlying a portion of the clip, said lateral side walls having spaced apart openings disposed therein in that portion of the mechanism on both side of said pivotal attachment, said articulating mechanism is a strap member attached at one end thereof to said pivotally attached distal end portion, said strap attachment being distally of said pivotal attachment, and the other end of said strap member being attached to said articulating knob, said distal end portion includes means for maintaining the relative positions of the clip storage an placement mechanism, the clip feed member and the jaw closure mechanism throughout articulation of the distal end portion, said handle assembly includes a single trigger means for actuating the jaw closure mechanism and the clip feed member and the articulating knob includes means to allow said strap member to rotate with the rotating assembly.

11. An articulating endoscopic surgical fastening instrument for applying a plurality of surgical fasteners in seriatim, said instrument comprising:

a) a handle portion;

b) an elongate hollow tubular portion extending distally from said handle portion;

c) a fastener applying head hingedly attached to the distal end of said hollow tubular portion for applying a surgical fastener;

d) articulating means attached to said fastener applying head for moving said fastener applying head in and out of longitudinal alignment with said hollow tubular portion;

e) feed means extending from said handle to said fastener applying head through said hollow tubular portion for feeding a fastener to said fastener applying head, said means being flexible at least in the area where said fastener applying head is hingedly attached to said hollow tubular portion;

f) actuating means extending from said handle to said fastener applying head to actuate said head to apply a fastener, said means being flexible at least in the area where said fastener applying head is hingedly attached to a said hollow tubular portion; and wherein a plurality of surgical fasteners are stored in said hollow tubular portion and the feed means feed said fasteners through the hinged attachment to the distal end of the fastener applying head.

12. An articulating endoscopic surgical fastening instrument according to claim 11 wherein the fastener applying head is pivotally attached to the hollow tubular portion.

13. An articulating endoscopic surgical fastening instrument according to claim 12 wherein the articulating means is attached to the fastener applying head distally of said pivot attachment.

14. An articulating endoscopic surgical fastening instrument according to claim 11 wherein the instrument is a multiple clip applier for applying surgical clips in seriatim to a vessel to be ligated and the fastener applying head includes a pair of jaws at the distal end thereof for holding and closing a surgical clip.

15. An articulating endoscopic surgical fastening instrument for applying a plurality of surgical fasteners in seriatim, said instrument comprising:

a) a handle portion;

b) an elongate hollow tubular portion extending distally from said handle portion;
c) a fastener applying head hingedly attached to the distal end of said hollow tubular portion for applying a surgical fastener;
d) articulating means attached to said fastener applying head for moving said fastener applying head in and out of longitudinal alignment with said hollow tubular portion;
e) feed means extending from said handle to said fastener applying head through said hollow tubular portion for feeding a fastener to said fastener applying head, said means being flexible at least in the area where said fastener applying head is hingedly attached to said hollow tubular portion;
f) actuating means extending from said handle to said fastener applying head to actuate said head to apply a fastener, said means being flexible at least in the area where said fastener applying head is hingedly attached to a said hollow tubular portion;
wherein the instrument is a multiple clip applier for applying surgical clips in seriatim to a vessel to be ligated and the fastener applying head includes a pair of jaws at the distal end thereof for holding and closing a surgical clip; and
wherein a plurality of surgical clips are stored in said hollow tubular portion and the feed means feed said clips through the hinged attachment to the jaws at the distal end of the fastener applying head.

16. A multiple clip applier according to claim 15 wherein the fastener applying head is pivotally attached to the hollow tubular portion.

17. A multiple clip applier according to claim 15 wherein the articulating means is attached to the fastener applying head distally of said pivot attachment.

18. An articulating endoscopic surgical instrument for applying a fastener to body tissue comprising;
a) an actuating mechanism;
b) an elongate hollow tubular portion extending distally from said actuating mechanism;
c) a hollow fastener applying head hingedly attached to the distal end of said elongate hollow tubular portion;
d) fastener applying means disposed at the distal end of said fastener applying head;
e) articulating means attached to said fastener applying head for moving said fastener applying head and said fastener applying means in and out of longitudinal alignment with said elongate hollow tubular portion;
f) feed means disposed in said elongate hollow tubular portion and extending into the fastener applying head for feeding a fastener to said fastener applying means;
g) drive means disposed in said elongate hollow tubular portion and extending to the fastener applying means to actuate said fastener applying means to place a fastener in body tissue; and
h) means disposed in said fastener applying head distally of said hinged attachment to maintain the relative position of the feed means and said drive means with respect to each other and with respect to said fastener applying means throughout all movement of said fastener applying head with respect to said elongate hollow tubular portion.

19. An articulating endoscopic surgical instrument according to claim 18 wherein the hollow fastener applying head is pivotally attached to the distal end of the elongate hollow tubular portion.

20. An articulating endoscopic surgical instrument according to claim 19 wherein the articulating means is attached to the fastener applying head distally of said pivot attachment.

21. An articulating endoscopic surgical instrument according to claim 18 wherein the instrument is a multiple clip applier for applying surgical clips to vessels to ligate the vessel and said fastener applying means comprises a pair of jaws for holding a surgical clip and said drive means closes the jaws to apply said clip to a vessel placed between said jaws.

22. An articulating endoscopic surgical instrument according to claim 21 wherein the hollow fastener applying head is pivotally attached to the distal end of the elongate hollow tubular portion and the articulating means is attached to the fastener applying head distally of said pivot attachment.

23. An articulating endoscopic surgical instrument according to claim 18 wherein the means for maintaining the relative positions of the feed means and the drive means comprises a pair of tracks disposed on the inside surface of the hollow fastener applying head, one of said pair of tracks engaging at least a portion of said feed means and the other of said pair of tracks engaging at least a portion of said drive means.

24. An articulating endoscopic surgical instrument according to claim 23 wherein the hollow fastener applying head is pivotally attached to the distal end of said elongate hollow tubular portion and the articulating means is attached to said fastener applying head distally of said pivotal attachment.

25. An articulating endoscopic surgical instrument according to claim 23 wherein the instrument is a multiple clip applier for applying surgical clips to vessels to ligate the vessel and said fastener applying means comprises a pair of jaws for holding a surgical clip and said drive means closes the jaws to apply said clip to a vessel placed between said jaws.

26. An articulating endoscopic surgical instrument according to claim 25 wherein the hollow fastener applying head is pivotally attached to the distal end of said elongate hollow tubular portion and the articulating means is attached to said fastener applying head distally of said pivotal attachment.

27. An articulating endoscopic multiple clip applier for applying a surgical clip to body tissue, said clip having a pair of legs and a connecting member joining said legs at one end of the clip, said applier comprising;
a) a handle portion;
b) a hollow elongate tubular portion extending distally from said handle portion;
c) a hollow clip applying head hingedly attached to the distal end of said hollow elongate tubular portion;
d) a pair of jaws for holding and closing a clip placed therebetween disposed at the distal end of said hollow clip applying head;
e) means attached to said clip applying head for moving said hollow clip applying head in and out of longitudinal alignment with said hollow elongate tubular portion;
f) an elongated clip storage track for housing an array of surgical clips in an end-to-end relationship, the proximal end of said track being disposed in the hollow elongate tubular portion and the distal end of the track extending into said hollow clip applying head, the portion of said clip track on both sides of said hinged attachment of the hollow clip applying head to the elongate tubular portion being flexible, said clip storage track including means for biasing the array of clips towards the distal end of said clip storage track;

g) a feed bar member mounted for reciprocation and disposed adjacent to and substantially parallel to said clip storage track throughout all movement of said hollow clip applying head;

g) spring means for placing the distal most clip from the clip track to in front of said feed bar member whereby said feed bar member can place said clip between said pair of jaws; and i) a jaw closure mechanism mounted for reciprocation and disposed adjacent and substantially parallel to said feed bar member throughout all movement of said hollow clip applying head.

28. An articulating endoscopic multiple clip applier according to claim 27 wherein the hollow clip applying head is pivotally attached to said hollow elongate tubular portion.

29. An articulating endoscopic multiple clip applier according to claim 28 wherein the means for moving said hollow clip applying head is attached to said head distally of said pivotal attachment.

30. An articulating endoscopic multiple clip applier according to claim 27 wherein the elongated clip storage track is a member having a rectangular cross-section defining a floor, lateral side walls, and a top overlying the legs of the clips, said lateral side walls having spaced apart openings disposed therein in that portion of the clip track on both sides of the hinged attachment of the hollow clip applying head to the elongate tubular portion.

31. An articulating endoscopic multiple clip applier according to claim 30 wherein the openings in the lateral side walls extend into the top of said clip track.

32. An articulating endoscopic multiple clip applier according to claim 31 wherein the portion of the openings in the top of the clip track are narrower than the portion of the openings in the lateral side walls.

33. An articulating endoscopic multiple clip applier according to claim 32 wherein the floor of the clip track has an opening therein, said opening extending for at least that portion of the clip track wherein there are openings in said lateral side walls.

34. An articulating endoscopic multiple clip applier according to claim 33 wherein the hollow clip applying head is pivotally attached to said hollow elongate tubular portion.

35. An articulating endoscopic multiple clip applier according to claim 34 wherein the means for moving said hollow clip applying head is attached to said head distally of said pivotal attachment.

36. An articulating endoscopic multiple clip applier according to claim 30 wherein the floor of the clip track has an opening therein on that portion of the clip track on both sides of the hinged attachment of the hollow clip applying head to the elongate tubular portion.

37. An articulating endoscopic multiple clip applier according to claim 30 wherein the hollow clip applying head is pivotally attached to said hollow elongate tubular portion.

38. An articulating endoscopic multiple clip applier according to claim 37 wherein the means for moving said hollow clip applying head is attached to said head distally of said pivotal attachment.

39. A rotatable articulating endoscopic fastening instrument for applying a surgical fastener to body tissue comprising;
   a) an actuation mechanism;
   b) an elongate rigid endoscopic portion extending distally from said actuation mechanism;
   c) a fastener applying head hingedly attached to the distal end of said rigid endoscopic portion;
   d) means for rotating the rigid endoscopic portion and the fastener applying head about the longitudinal axis of the same, said rotating means comprising a rotatable knob mounted on said rigid endoscopic portion at the proximal end thereof and, said rotatable knob connected to said rigid endoscopic portion so that on rotation of said knob said rigid endoscopic portion rotates therewith;
   e) articulating means for moving said fastener applying head in and out of longitudinal alignment with said rigid endoscopic portion, said articulating means comprising a member having an end thereof attached to said fastener applying head with the other end of said member extending to the proximal portion of said rigid endoscopic portion and an articulating knob mounted for rotation on said rigid endoscopic portion, said knob comprising a first circular portion having its inside surface threaded and a second circular portion fitting inside said first circular portion and having its outside surface threaded to mesh with the threads on the inside surface of said first circular portion whereby when said first circular portion is rotated, said second circular portion moves longitudinally; and
   f) means for allowing articulation of the fastener applying head at any rotational position of the rigid endoscopic portion, said means for allowing articulation comprising a connecting member having its distal end attached to said articulating means member and its proximal end attached to said second circular portion to allow rotation of said articulating means member with respect to said second circular portion and movement of said articulating means member longitudinally with the longitudinal movement of said second circular portion.

40. A rotatable articulating endoscopic fastening instrument according to claim 39 wherein said fastener applying head is pivotally attached to the rigid endoscopic portion.

41. A rotatable articulating endoscopic fastening instrument according to claim 40 wherein the end of the flexible member attached to said fastener applying head is attached distally of said pivot attachment.

42. A rotatable articulation endoscopic fastening instrument according to claim 39 wherein the instrument is a multiple clip applier for applying a plurality of surgical clips in seriatim to body tissue and the feed applying head includes a pair of jaws disposed at the distal end of said head for grasping and applying a surgical clip to body tissue.

43. A rotatable articulating multiple clip applier according to claim 39 wherein said fastener applying head is pivotally attached to the rigid endoscopic portion and the articulating means attached to said fastener applying head is attached distally of said pivot attachment.

* * * * *